US00H002234H

(19) United States
(12) Statutory Invention Registration
Mazzell et al.

(10) Reg. No.: US H2234 H
(43) Published: Jan. 5, 2010

(54) PURIFICATION OF DESFLURANE CONTAINING R-123

(75) Inventors: Paul Mazzell, Aiken, SC (US); Peter Murin, River Edge, NJ (US)

(73) Assignee: Halocarbon Products Corporation, River Edge, NJ (US)

(21) Appl. No.: 11/400,453
(22) Filed: Apr. 7, 2006
(51) Int. Cl.
*A61M 15/00* (2006.01)

(52) U.S. Cl. ..... 128/203.12
(58) Field of Classification Search ..... 128/203.12
See application file for complete search history.

*Primary Examiner*—Michelle Clement
(74) *Attorney, Agent, or Firm*—Kurt G. Briscoe; Norris McLaughlin & Marcus, P.A.

(57) ABSTRACT

A process for preparing 2-difluoromethoxy-1,1,1,2-tetrafluoroethane (desflurane) comprising the following steps:

(a) providing a first mixture comprising desflurane and 2,2-dichloro-1,1,1-trifluoroethane (R-123);

(b) adding water to the first mixture to form a second mixture; and (c) fractionally distilling the second mixture to yield a desflurane product purer in R-123 than said the mixture.

Also described is a purified desflurane product prepared by the process, and intermediate products comprising water added to a mixture of desflurane and R-123.

11 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PURIFICATION OF DESFLURANE CONTAINING R-123

BACKGROUND OF THE INVENTION

1. Field of the Invention

The present invention relates to the purification of 2-difluoromethoxy-1,1,1,2-tetrafluoroethane (desflurane), which is a well known inhalation anesthetic.

2. Description of Related Art

U.S. Provisional Application No. 60/643,301 describes a process for the preparation of desflurane by reaction of 2-chloro-2-difluoromethoxy-1,1,1-trifluoroethane (isoflurane) with hydrogen fluoride (HF) over a fixed bed catalysts. This process has a number of advantages in that it is greener than previous processes, highly efficient and adaptable to a continuous process.

Even though this process also yields desflurane of a purity well within the specifications for anesthetic grade desflurane, the product contains a very small amount of 2,2-dichloro-1,1,1-trifluoroethane (R-123) as a by-product. Since R-123 and desflurane have similar boiling points (27° C. ) and 23° C., respectively) it is not easy to separate the R-123 from the desflurane by distillation.

Nevertheless, the ability to remove the R-123 would afford an even purer product. Accordingly, we have endeavored to reduce the R-123 content in the desflurane product.

SUMMARY OF THE INVENTION

This and other objects were met with the present invention, which in a first embodiment relates to a process comprising the following steps:

(a) providing a first mixture comprising desflurane and R-123;

(b) adding water to said first mixture to form a second mixture; and (c) fractionally distilling said second mixture to yield a desflurane product purer in R-123 than said first mixture.

The present invention relates in a second embodiment to said second mixture comprising desflurane, R-123 and said added water.

The present invention also relates in a third embodiment to said purer desflurane product obtainable as a result of the inventive process.

DETAILED DESCRIPTION OF THE INVENTION

The first mixture comprising desflurane and R-123 is obtainable from any suitable source and in any suitable manner. In a preferred embodiment, the mixture of desflurane and R-123 already meets the specifications for anesthetic grade desflurane, i.e., the amount of R-123 is sufficiently small that the overall desflurane product meets anesthetic grade desflurane specifications. In a particularly preferred embodiment, the amount of R-123 is 1% by weight or less based on the total weight of the first mixture. In an especially preferred embodiment, the first mixture is prepared by the process described in U.S. Provisional Application Ser. No. 60/643,301, the entire contents of which are hereby incorporated herein by reference. All embodiments described therein are suitable, and are considered described herein as methods for preparing the first mixture.

The amount of water added to form the second mixture can be varied over a relatively wide range. Preferably, the amount of water is 1 to 100% by weight based on the total weight of the first mixture. Especially preferred are embodiments wherein the amount of water is 3 to 15% by weight based on the total weight of the first mixture.

The distillation of the second mixture can be carried out according to techniques well known in the art. Pressure is not critical, and the distillation can be carried out at reduced pressure, at atmospheric pressure or at elevated pressure. Preferably, the distillation is carried out at elevated pressure, especially at 5 to 175 psi.

In a preferred embodiment, the purer desflurane product obtainable by the inventive process has less than 200 ppm of R-123 impurity. In a particularly preferred embodiment, the amount of R-123 is less than 40 ppm, and very preferably less than 5 ppm. In an especially preferred embodiment, the amount of R-123 is less than 3 ppm, or less than 2 ppm, or even less than 1 ppm.

The invention will now be described in greater detail with reference to the following non-limiting example:

EXAMPLE

To 28.5 kg of desflurane obtainable from the process described in Provisional Application Ser. No. 60/643,301 is added 2.5 kg of water. The mixture is then allowed to reflux for duration shown in the following table and both the overhead (O/H) and bottoms (B) samples are obtained and analyzed using GC.

| Sample | After Refluxing Hrs. | Desflurane | R-123 |
|---|---|---|---|
| S/M | — | 99.46% | 0.33% |
| O/H | 7 hrs. | 91.69% | 8.25% |
| B | 7 hrs | 99.97% | 168 ppm |
| O/H | 13 hrs. | 92.63% | 7.32% |
| B | 13 hrs | 99.98% | 39 ppm |
| O/H | 16 hrs. | 92.98% | 6.98% |
| B | 16 hrs | 99.99% | 21 ppm |
| O/H | 23 hrs. | 94.89% | 5.08% |
| B | 23 hrs | 99.99% | <1 ppm |

The column is locked off and drained, the material in the pot is distilled and fractions are collected after distilling 4 kg, 12 kg, 16 kg and 22 kg. These fractions are then analyzed using GC. Finally the total amount of material collected is analyzed. The results are shown in the table below.

| Sample | After T/O | Des | R-123 |
|---|---|---|---|
| 1 | 4 kg | 99.999% | 3 ppm |
| 2 | 12 kg | 99.997% | 3 ppm |
| 3 | 16 kg | 99.999% | <2 ppm |
| 4 | 21 kg | 99.999% | <2 ppm |
| Collection Receiver (21.5 kg) | | 99.999 | 3 ppm |

It should be understood that the preceding detailed description of the invention is merely a detailed description of one preferred embodiment or of a small number of preferred embodiments of the present invention and that numerous changes to the disclosed embodiment(s) can be made in accordance with the disclosure herein without departing from the spirit or scope of the invention. The preceding detailed description of the invention, therefore, is not meant to limit the scope of the invention in any respect.

What is claimed is:

1. A process for preparing 2-difluoromethoxy-1,1,1,2-tetrafluoroethane (desflurane) comprising the following steps:

(a) providing a first mixture comprising desflurane and 2,2-dichloro-1,1,1-trifluoroethane (R-123);

(b) adding water to said first mixture to form a second mixture; and (c) fractionally distilling said second mixture to yield a desflurane product purer in R-123 than said first mixture.

2. The process according to claim 1, wherein said first mixture comprises 1% or less by weight of R-123.

3. The process according to claim 1, wherein the first mixture is an anesthetic grade desflurane.

4. The process according to claim 1, wherein the amount of water added to said first mixture is 1 to 100% by weight based on the total weight of the first mixture.

5. The process according to claim 4, wherein the amount of water added to said first mixture is 3 to 15% by weight based on the total weight of the first mixture.

6. A composition of matter comprising:

(a) desflurane;

(b) R-123; and (c) water.

7. The composition according to claim 6, which contains 1 to 100% by weight of water based on the total weight of the combination of desflurane and R-123.

8. The composition according to claim 7, which contains 3 to 15% by weight of water based on the total weight of the combination of desflurane and R-123.

9. A composition of matter comprising desflurane in admixture with R-123, wherein the amount of R-123 is less than 200 ppm.

10. The composition according to claim 9, wherein the amount of R-123 is less than 40 ppm.

11. The composition according to claim 10, wherein the amount of R-123 is less than 5 ppm.

* * * * *